US011576416B2

United States Patent
Bleiel et al.

(10) Patent No.: US 11,576,416 B2
(45) Date of Patent: Feb. 14, 2023

(54) METHOD OF PRODUCING MICROPARTICLES OF THE TYPE HAVING A CROSSLINKED, AGGREGATED PROTEIN MATRIX BY SPRAY DRYING

(71) Applicant: Anabio Technologies Limited, Dublin (IE)

(72) Inventors: Sinead Bleiel, Dublin (IE); Maria Luz Perez Gomez de Cadinanos, County Cork (IE); Robert Kent, County Cork (IE)

(73) Assignee: Anabio Technologies Limited, Dublin (IE)

( * ) Notice: Subject to any disclaimer, the term of this patent is extended or adjusted under 35 U.S.C. 154(b) by 838 days.

(21) Appl. No.: 16/441,841

(22) Filed: Jun. 14, 2019

(65) Prior Publication Data

US 2019/0289896 A1     Sep. 26, 2019

Related U.S. Application Data

(63) Continuation of application No. 15/564,632, filed as application No. PCT/EP2016/061622 on May 23, 2016, now abandoned.

(30) Foreign Application Priority Data

May 21, 2015    (GB) .................................... 1508745

(51) Int. Cl.
     *A23P 10/40*        (2016.01)
     *C08J 3/12*         (2006.01)
     (Continued)

(52) U.S. Cl.
     CPC .............. *A23P 10/40* (2016.08); *A23L 29/20* (2016.08); *A23L 29/238* (2016.08);
     (Continued)

(58) Field of Classification Search
     CPC .............................. A23P 10/40; A61K 9/4833
     See application file for complete search history.

(56) References Cited

U.S. PATENT DOCUMENTS

2014/0348815 A1    11/2014   Jeoh-Zicari et al.

FOREIGN PATENT DOCUMENTS

| | | |
|---|---|---|
| EP | 1 514 538 | 3/2005 |
| EP | 2 868 206 | 5/2015 |

(Continued)

OTHER PUBLICATIONS

Vemmer et al., "Review of encapsulation methods suitable for microbial biological control agents", Biological Control, 67, (2013), pp. 380-389. (Year: 2013).*

(Continued)

*Primary Examiner* — Elizabeth Gwartney
(74) *Attorney, Agent, or Firm* — Cesari & McKenna, LLP

(57) ABSTRACT

A method of producing microparticles by spray drying comprises the steps of providing a spray-drying feedstock solution comprising water, a volatile divalent metal salt, weak acid, 5-15% dairy or vegetable protein (w/v) and 1-20% active agent (w/v). The feedstock solution is adjusted to have a pH at which the volatile divalent metal salt is substantially insoluble. The feedstock solution is then spray-dried at an elevated temperature to provide atomised droplets, whereby the volatile divalent metal salt disassociates at the elevated temperature to release divalent metal ions which crosslink and aggregate the protein in the atomised droplets to produce microparticles having a crosslinked aggregated protein matrix and active agent dispersed throughout the matrix.

17 Claims, 14 Drawing Sheets

(51) Int. Cl.
| | |
|---|---|
| *A23L 33/185* | (2016.01) |
| *A23L 33/19* | (2016.01) |
| *A23L 29/238* | (2016.01) |
| *A23L 29/256* | (2016.01) |
| *H01M 10/42* | (2006.01) |
| *A23L 29/20* | (2016.01) |
| *H02J 7/34* | (2006.01) |
| *A61M 15/06* | (2006.01) |
| *A61M 11/04* | (2006.01) |
| *H01M 10/0525* | (2010.01) |

(52) U.S. Cl.
CPC ........... *A23L 29/256* (2016.08); *A23L 33/185* (2016.08); *A23L 33/19* (2016.08); *C08J 3/122* (2013.01); *H01M 10/42* (2013.01); *H02J 7/345* (2013.01); *A23V 2002/00* (2013.01); *A23V 2200/228* (2013.01); *A23V 2250/282* (2013.01); *A23V 2250/506* (2013.01); *A23V 2250/5036* (2013.01); *A61M 11/042* (2014.02); *A61M 15/06* (2013.01); *C08J 2389/00* (2013.01); *H01M 10/0525* (2013.01)

(56) References Cited

FOREIGN PATENT DOCUMENTS

| | | |
|---|---|---|
| GB | 2 388 581 | 11/2003 |
| WO | WO 2009/062254 | 5/2009 |

OTHER PUBLICATIONS

Ain Riaz et al., "Recent Trends and Applications of Encapsulating Materials for Probiotic Stability", Critical Reviews in Food Science and Nutrition, 52, (2013), pp. 231-244. (Year: 2013).*

* cited by examiner

| Divalent Salts | Formula | Mw |
|---|---|---|
| Calcium chloride | $CaCl_2 2H_2O$ | 147.02 |
| Calcium glycerophosphate | $C_3H_7CaO_6P$ | 210.14 |
| Calcium lactate | $CaC_6H_{10}O_6$ | 218.23 |
| Calcium Triphosphate | $Ca_3O_8P_2$ | 310.19 |
| Magnesium chloride | $MgCl_2 6H_2O$ | 203.31 |
| Magnesium sulfate | $MgSO_4 7H_2O$ | 246.48 |
| Zinc chloride | $ZnCl_2 2H_2O$ | 136.30 |
| Zinc sulfate | $ZnSO_4 7H_2O$ | 287.56 |

FIG. 3.

| Salt Concentration/ Mixtures therof | Weak Acid | Observation of Solubility |
|---|---|---|
| 0.4M | 0.80M | Clear |
| 0.4M | 1.00M | Clear |
| 0.6M | 1.40M | Clear |
| 0.6M | 0.90M | Turbid |
| 0.8M | 1.65M | Clear |
| 0.8M | 1.20M | Turbid |
| 0.8M | 1.40M | Clear |
| 0.1M | 0.25M | Clear |
| 0.15M | 0.45M | Clear |
| 0.15M | 0.60M | Turbid |
| 0.20 M | 0.60M | Clear |

FIG. 4.

| Solution | Total Weight | Pellet Weight | % inSolubles |
|---|---|---|---|
| Before Drying | | | |
| Native Protein + H2O | 974.6 | 97.9 | 10.05% |
| Hydrolysed Protein + EDTA | 939.6 | 89.0 | 9.4% |
| Native Protein + Acid + Ca Salt + EDTA | 960.2 | 94.4 | 9.83% |
| After Drying | | | |
| Native Protein + H2O | 943.0 | 85.7 | 9.08% |
| Hydrolysed Protein + EDTA | 924.3 | 124.0 | 13.42% |
| Native Protein + Acid + Ca Salt + EDTA | 954.4 | 210.7 | 22.08% |

Fig. 14.

METHOD OF PRODUCING MICROPARTICLES OF THE TYPE HAVING A CROSSLINKED, AGGREGATED PROTEIN MATRIX BY SPRAY DRYING

CROSS REFERENCE TO RELATED APPLICATIONS

This application is a continuation of U.S. patent application Ser. No. 15/564,632, filed on Oct. 5, 2017, now abandoned, which is the National Stage of International Application No. PCT/EP2016/061622, filed on May 23, 2016, which claims the benefit of Great Britain Application No. 1508745.5, filed on May 21, 2015. The contents all prior applications are hereby incorporated by reference in their entirety.

TECHNICAL FIELD

The invention relates to method of producing microparticles by spray drying, especially microparticles of the type having a crosslinked and aggregated protein matrix in which the protein is of dairy or vegetable origin.

BACKGROUND TO THE INVENTION

The disintegration of liquid into small droplets have long been a significant field of research interest, due to two reasons: (1) to apply to a liquid in some unit operations (particularly drying, cooling or freezing) and 2) to produce granular/capsular materials that offer some advantages such as stability, ease of dosing/handling and specific processing surface characteristics. This disintegration of liquid into droplets is evident in the field of micro-encapsulation where a core material (i.e. bioactive) is inserted or entrapped in a matrix (for example, WO2010119041) for improved bioactive protection, product yield and also to facilitate subsequent production processes. Examples of such encapsulation methods include emulsification, fluidized-bed coating, laminar jet breakup, coacervation, liposomes, complexation, crystallization and spray-drying. Most of these methods require the disintegration of a liquid, which can be done by a large number of techniques such as pressure atomization by pressure nozzles or two-fluid gas-stream atomization usually with air or steam as the atomising fluid.

Laminar jet breakup (i.e. production of micro-particles) and spray-drying (i.e. atomization by rotating disc) both remain the most promising processing technologies for the food and feed industry since conditions are mild, there is no significant problem of blockages/plugging and the processes are continuous and commercially viable. For example, methods of producing microparticles (using laminar jet breakup) having dairy protein matrices are well known and described in, for example, WO2010119041 (Teagasc). Generally, these types of microparticles are produced by providing a suspension of denatured protein, for example whey protein, and an active agent, treating the suspension to provide microdroplets using a vibrating nozzle, and then immediately immersing the microdroplets in an acidification bath to gel and solidify the microdroplets. While this method produces spherical, homogenously-sized microdroplets that are capable of gastric transit intact, the process involves use of specialised vibrating nozzle machinery which represents an additional expense for food companies. There is therefore a desire amongst food/feed producers and especially milk producers for a method of producing such microparticles using conventional food processing machinery such as spray dryers (See FIG. 1 schematic). Furthermore, this technology also requires a pre-heating step for the preparation of denatured protein. This pre-denaturation step can indeed be incorporated into industrial operations for value-added products; however, manufacturers of commodity/lower value products continue to seek practical and direct routes for the stabilisation of lower market value materials. Furthermore, the drying of microbeads generated by the technology WO2010119041 is not easily achieved using spray drying technology since the relatively large size of the micro-beads causes a disruption of the atomisation processes. In order to avoid deposits of wet and sticky micro-beads on the drier wall (See FIG. 2), micro-beads must be completely dry before they make contact with the interior wall of the drying chamber. Hence, micro-bead trajectories must be kept away from the drying chamber wall for longest time possible to allow correct drying; however this is not practically possible for commercial spray-drying scenarios.

Spray drying is a suspended particle dryer technique consisting of three essential steps: i) atomization, where the droplets are formed; ii) drying gas and droplet contact, where the liquid feed is turned into droplets; and finally iii) powder recovery, where the dried particles are separated from the drying gas stream. The use of a spray dryer to produce microparticles for bioactive stabilisation would involve re-designing of the micro-bead production process (WO2010119041), as it is not possible or appropriate to employ an acidification bath with spray dried particles, as the particles are dehydrated and atomised in the drying chamber.

A principal objective in drying involves the assurance that the liquid comes to disc speed and to obtain a uniform drop size distribution in the atomised liquid. However, the readjustment of shear stresses within the liquid once the droplet is airborne is another factor contributing to further disintegration of the droplet/microparticle. This is again a limitation for microbead technologies using spray-drying. To date, there is almost no records or publication on the area required for the collection of cross-linked & aggregated particles from the rotating disc in good conditions. In comparison to lyophilisation, spray drying is generally more flexible, more efficient and more economical in terms of installation, investment and operation for the same evaporative capacity. For instance, the evaporative capacity of a normal sized pharmaceutical spray dryer can match the evaporative capacity of 5-7 large freeze dryers. In many cases, however, the two technologies are supplementary. For small batches of difficult-to-dry powders to be supplied in vials, lyophilisation has an advantage, whereas spray drying has an advantage if free flowing powders are required. For this reason, the stabilisation of bioactive material using spray drying is a field with huge interest.

To summarise, spray-drying of protein feedstock solutions produces very small particles, too small to be able to entrap active agents such as probiotic cells (See FIGS. 5 and 6). One possible solution to this problem is replacement of an atomiser nozzle in a spray dryer with a vibrating nozzle, however this approach resulted in large droplets that stuck to the dryer wall (FIG. 2). A further possible solution is to add a cross-linking agent to the liquid feedstock with a view to making larger spray-dried particles that consist of cross-linked protein, however this results in cross-linking of the protein in the feedstock liquid prior to atomisation, with a resultant increase in viscosity and in most cases gelation of the feedstock liquid making it impossible to atomise the feedstock solution.

US2014/348815 discloses a method of producing microparticles by spray-drying that employs sodium alginate as a polymer for making the microparticle matrix, and employs a feedstock comprising a volatile base such as ammonia hydroxide or other volatile amines such as hydrazines, methylamine, trimethylamine, or ethylamine. The use of such volatile bases would prevent the microparticles being classified as food-grade products. Moreover, as alginate is such a strong gelling agent, only very low amounts can be employed in spray-drying feedstock which means that the total solids of the resultant microparticles is quite low, resulting in less polymerisation of the matrix and consequently a weaker and less stable matrtix, reduced yield of active agent (cargo) during drying, and less control of particle size.

It is an object of the invention to overcome these problems. It is a particular object of the invention to provide a method of producing food grade active-containing microparticles by means of conventional spray-drying that have greater yields that the methods of the prior art.

STATEMENTS OF INVENTION

The Applicant has overcome the problems set out above by providing a liquid feedstock solution comprising protein, acid, and a crosslinking agent in an inactive precursor form that is activated in the elevated temperature conditions of the drying chamber to release a divalent metal crosslinking agent which crosslinks and aggregates the protein at the atomised droplet stage. The precursor crosslinking agent is a volatile divalent metal salt that is insoluble in the feedstock and which dissociates at elevated dryer temperatures to release the divalent metal ion which is an active crosslinking agent. The feedstock includes a weak acid which maintains the pH of the feedstock above the pH at which the volatile divalent metal salt solubilises, and obviates the need for a volatile base. The use of dairy or vegetable protein as a matrix forming agent (as opposed to alginate) allows the formulation of spray-drying feedstocks with greater total solids content, and consequently greater levels of matrix polymerisation with resultant improvement in microparticle stability and yield. In particular, the use of the method of the invention allows the production of microparticles having an active agent yield of 50% to more than 80% of the microparticle (w/w), which is a significant improvement compared to the methods of the prior art which achieve about 11%-13% yield of active (cargo).

Thus, in a first aspect, the invention provides a method of producing microparticles by spray drying, the method comprising the steps of:
  providing a spray-drying feedstock solution comprising water, a volatile divalent metal salt, weak acid, protein (for example 5-15% w/v), and active agent (for example 1-20% w/v), the feed solution having a pH at which the volatile divalent metal salt is substantially insoluble;
  spray drying the feedstock solution at an elevated temperature to form atomised droplets whereby the volatile divalent metal salt disassociates at the elevated temperature to release divalent metal ions which crosslink and subsequently aggregate the protein in the atomised droplets to produce microparticles having a crosslinked aggregated protein matrix and active agent dispersed throughout the matrix.

In one embodiment, the feedstock comprises a hydrocolloid. This allows for the formation of a matrix protein-hydrocolloid polymerised cross-linked matrix which has been demonstrated to provide a stronger matrix and consequent improved stability of the active agent.

The invention also provides a liquid feedstock suitable for spray-drying and comprising water, a volatile divalent metal salt, weak acid, protein (for example 5-15% w/v), and active agent (for example 1-20% w/v), the feed solution having a pH at which the volatile divalent metal salt is substantially insoluble.

It will be appreciated that the amount of weak acid, salt and protein can be varied but generally 5-15% protein (w/v) is employed, and the concentration of weak acid and salt can be adjusted to ensure that the salt is insoluble in the feedstock suspension and that there is sufficient salt to cause crosslinking and aggregation of the protein in the atomised droplet in the drying chamber. Typically, a 0.2 to 2.2M aqueous weak acid solution is employed in the feedstock. Typically, a 0.1 to 2.0M suspension of volatile divalent metal salt is employed in the feedstock.

Typically, the pH is acidic and typically a salt is employed that is insoluble at acidic pH. In one embodiment, the pH of the feedstock solution is at least 6. In one embodiment, the pH of the feedstock solution is at least 7. In one embodiment, the pH of the feedstock solution is at least 8. In one embodiment, the pH of the feedstock solution is from 5 to 8. In one embodiment, the pH of the feedstock solution is from 6 to 8. In one embodiment, the pH of the feedstock solution is about 7.

In one embodiment, the volatile divalent metal salt comprises a divalent metal ion selected from calcium, zinc or magnesium. In one embodiment, the volatile divalent metal salt comprises a volatile anion selected from chloride, phosphate, carbonate, citrate, ascorbate or mixtures thereof. Mixtures of various calcium sources are commonly found in infant formula applications. In one embodiment, the volatile divalent metal salt comprises a plurality of different salts, for example a calcium salt plus a magnesium salt, or a calcium carbonate plus a calcium chloride. In one embodiment, the volatile divalent metal salt comprises a mixture of calcium carbonate, calcium triphosphate, and calcium chloride.

Preferably, the weak acid is selected from ascorbic acid, acetic acid or succinic acid. In one embodiment, the weak acid comprises a mixture of weak acids, for example acetic acid plus ascorbic acid, or ascorbic acid plus succinic acid.

Preferably, the protein is selected from dairy protein (i.e. whey or casein), egg protein, vegetable protein or mixtures thereof.

Preferably, the dairy protein is selected from casein, or whey protein. Sources of casein include UHT milk and skim milk powder. Sources of whey protein include Whey Protein Isolate (WPI).

Preferably, the vegetable protein is selected from pea protein, rice protein or wheat protein (gluten).

Preferably, the feedstock dispersion has a solids content of 30-70%, preferably 40-60%, more preferably 45-55%, and ideally approximately 50%.

Preferably, the spray-drying feedstock solution is prepared by the sequential steps of:
  preparing an aqueous solution of weak acid;
  preparing an aqueous dispersion of volatile divalent metal salt;
  mixing the solution and dispersion to provide a weak acid/volatile divalent metal salt dispersion and adjusting the pH such that the volatile divalent metal salt is substantially insoluble;
  preparing an aqueous dispersion of protein;

admixing the active agent with the aqueous dispersion of protein to provide an active agent/protein dispersion; and admixing the active agent/protein dispersion and weak acid/volatile divalent metal salt dispersion, typically at a ratio of 1.0:1.5 to 1.5:1.0, to form the spray-drying feedstock solution.

Preferably, the aqueous solution of weak acid has a weak acid concentration of 0.2 M-2.2 M (2%-20%).

Preferably, the volatile divalent metal salt has a volatile divalent metal salt concentration of 0.1 M-2.0 M (1%-20%).

Preferably, the aqueous dispersion of protein has a protein concentration of 4-15% (w/v).

Preferably, the active agent/protein dispersion and weak acid/volatile divalent metal salt solution are mixed at a ratio of 1.0:1.5 to 1.5:1.0 to form the spray-drying feed solution. In one embodiment, the feedstock solution comprises hydrocolloid. Typically, some of the protein is replaced by hydrocolloid. This has been found to improve capsule strength and help prevent or inhibit moisture migration into the microparticles, due to hydrocolloid induced increases in polymerisation. In particular, the use of hydrocolloids in the feedstock allows for a higher solids content in the drier, which delivers a more efficient commercial production and enhanced commercial production yield. Thus, for example, the feedstock may comprise 10% protein and 5% hydrocolloid. Typically, the feedstock solution comprises 0.1 to 10.0% hydrocolloid (w/v), preferably 1-7% (w/v), and ideally 1-5% (w/v). In one embodiment, the hydrocolloid is selected from FOS, GOS, inulin, carrageenan and guar gum.

The invention also provides a spray-dried microparticle having an active agent homogenously dispersed throughout a continuous protein matrix, in which the protein matrix comprises agglomerated and divalent metal ion crosslinked protein. In one embodiment, the microparticle comprises hydrocolloid. In one embodiment, the hydrocolloid is selected from FOS, GOS, inulin, carrageenan and guar gum. In one embodiment, the microparticle has a dimension of less than 100 microns, for example 29-90 microns.

In one embodiment, the microparticle comprises at least 50%, 60%, 70% or 80% active agent (w/w). In one embodiment, the microparticle comprises at least 50% active agent (w/w), in which the active agent is a cell. In one embodiment, the microparticle comprises at least 70%, active agent (w/w) in which the active agent is non-cellular, for example a compound.

Typically, the protein comprises dairy protein, vegetable protein, or a mixture of dairy protein and vegetable protein.

Typically, the spray-dried microparticle of the invention is capable of surviving gastric transit in a mammal in an intact form. Preferably the mammal is a human. See FIG. 13. In one embodiment, the feedstock (or the microparticle) does not comprise a hydrophobic compound.

Definitions

"Microparticle" means a particle having an average dimension of 10-250 microns as determined by electron microscopy or standard size distribution analysis having a protein matrix crosslinked and aggregated by divalent metal ions. Typically the microparticles has a monodispersed matrix, which means that the components of the microparticle are homogenously mixed in a single phase. This is distinct and different from microcapsules having a core-shell morphology. In one embodiment, the microparticle has an average dimension of 10-80 microns. In one embodiment, the microparticle has an average dimension of 10-60 microns. In one embodiment, the microparticle has an average dimension of about 20 to about 50 microns.

"Food grade" as applied to a spray-drying feedstock or microparticle means that all the components in the feedstock or microparticle are food grade, i.e. suitable for oral ingestion by humans.

"Spray drying" is a quintessential preservation and encapsulation method for active agents, such as peptides, micronutrients, starter cultures, probiotics and biological cells lines with poor viability characteristics. Most spray dryers consist of feed pump, atomizer, air heater, air disperser, drying chamber, and systems for exhaust air cleaning and powder recovery (FIG. 1).

"Feedstock solution" or "Liquid feedstock" means the liquid mixture of components that are fed to the atomiser in the spray dryer. Some of the components will be soluble and some insoluble and homogenously dispersed. It generally comprises water, protein, weak acid and volatile divalent metal salt in an insoluble dispersed form. The water and weak acid may be combined into an aqueous solution of weak acid. The first step in the spray drying process of the invention is to prepare the feedstock for spraying by optimizing the temperature, concentration, viscosity or other characteristics. Typically, the method of preparing the feedstock comprises preparation of a weak acid/salt dispersion, preparation of a protein/active agent solution/dispersion, and mixture of the acid/salt dispersion with the protein/active solution or dispersion.

"Rotary atomization" can be defined as a disintegrating system where the feed liquid is distributed centrally on a wheel, disc or cup, and centrifugally accelerated to a high velocity before being discharged as droplets into the surrounding air-gas atmosphere.

"Solids content" means the percent of the feedstock that is composed of solids. Most feedstock has approx. 50% solids, although the range is from about 15% to 70%. Increasing the solids content reduces the amount of moisture removed in the spray drying process. As the solids content increases, the feedstock becomes more difficult to pump and atomize.

"Volatile divalent metal salt" means a salt formed between a divalent metal cation, typically a food grade cation such as calcium, and a volatile anion such as a carbonate. The term "volatile anion" means an anion forming part of a salt that vaporises at spray drying chamber temperatures, for example a temperature of greater than 80° C., for example 80-190° C. Examples of volatile divalent metal salts include calcium chloride tricalcium phosphate (commonly known as CTP), calcium citrate, calcium ascorbate, calcium carbonate, calcium HMB (hydroxymethyl butyrate), magnesium phosphate, magnesium carbonate, magnesium citrate, magnesium ascorbate, magnesium HMB, zinc phosphate, zinc carbonate, gluconate; lactate, glycerophosphate, divalent metal HMB, and mixture thereof (See Table 1). Zinc compounds have higher astringency values and a glutamate-like sensation; and bitterness is known to be pronounced for magnesium and calcium salts. Bitterness was affected by the anion in calcium salts.

"The feedstock solution having a pH at which the volatile divalent metal salt is substantially insoluble" should be understood to mean a pH at which the salt is in a dispersed, non-solubilised, form. Most volatile divalent metal salts are insoluble at acidic pH, therefore the pH of the feedstock is generally acidic. However, in some embodiments, for example when calcium triphosphate is employed, the pH of the feedstock may be lower than 7, for example above 5.

"Viscosity" means the resistance to flow of fluids. The most commonly used unit is the centipoise. Increasing viscosity tends to increase droplet size. For some nozzle designs, increasing the viscosity tends to increase the flow rate.

"Weak acid" means an acid that dissociates incompletely, releasing only some of its hydrogen atoms into the solution. Hence, it is less capable than a strong acid of donating protons. These acids have higher pKa than strong acids, which release all of their hydrogen atoms when dissolved in water.

"Protein" means a dairy protein (i.e. casein or whey) or diary protein preparation (SMP or WPI) or a vegetable protein (pea) or vegetable protein preparation, or mixtures thereof. In a preferred embodiment, the protein comprises a mixture of a dairy protein and vegetable protein. The protein may be provided intact (non-hydrolysed) or partially or fully hydrolysed form.

"Intact protein" in this context is interpreted as non-hydrolysed protein. This means that the protein bonds in the intact protein fraction should be intact, i.e. a degree of hydrolysis (DH) of 0%. The Degree of Hydrolysis (DH) may be determined using a rapid OPA test (Nielsen, P. M.; Petersen, D.; Dambmann, C. Improved method for determining food protein degree of hydrolysis. Journal of Food Science 2001, 66, 642-646). The invention therefore relates to a composition as described above wherein the delivery vehicle comprises between 1% or 100% intact protein as a fraction of the total protein content of the particles.

"Active agent" should be understood to encompass any molecule, compound, complex, organelle, or cell, in any form, that would benefit from being protected within a protein matrix. Typically, the active agent confers a beneficial effect or pharmacological activity upon interaction with any cell, tissue or organ of a mammal. The active agent can compromise of probiotic cells, bacteria, yeasts, enzymes, colours, vitamins, minerals, flavours, hydrophobic peptides, vaccines (mycoplasma) and mixtures thereof. Examples of active agents include cells (i.e. probiotic cells or stem cells), compounds (i.e. vitamins or minerals), complexes (HDAC inhibitors) proteins or peptide (i.e. insulin, VEGF), antibodies (i.e. therapeutic antibodies), nucleic acid (i.e. miRNA, siRNA, genes, vectors, plasmids), drugs (protein-based drugs such as Angiogenin). In one embodiment, the active agent is a cell. In one embodiment, the active agent is a vitamin (for example, a water soluble vitamin such as Vitamin C). In one embodiment, the active agent is a cell, and comprises 1-20% of the feedstock (w/v). In one embodiment, the active agent is a compound, and the active agent comprises 1-60% of the feedstock (w/v). In one embodiment, the active agent is a compound, and the active agent comprises 10-50% of the feedstock (w/v). In one embodiment, the active agent is a compound, and the active agent comprises 30-50% of the feedstock (w/v).

"pKa" means the acid dissociation constant, $K_a$, (also known as acidity constant, or acid-ionization constant) is a quantitative measure of the strength of an acid in solution.

"Dairy protein" means any protein source isolated from expressed from the mammary glands of a female mammal. Dairy proteins include any of the following:

- Casein is one of two major groups of protein present in milk. The action of rennet on casein during the manufacture of cheese results in the separating of milk into curds and whey. Casein forms the cheese while the whey proteins go into the whey stream. Sodium caseinate is the final end product from this process stream.
- Milk protein concentrate (MPC)-Milk protein concentrates are produced by ultrafiltration (UF) of milk. The product in liquid form is generally referred to as UF milk while the dry form is known as MPC. This product contains unaltered forms of both casein and whey protein. The level of protein, lactose and mineral present vary depending on the degree of protein concentration.
- Nonfat dry milk (NFDM)-Nonfat dry milk or skim milk powder is skim milk with the water removed. The composition of the original skim milk is not altered.
- Skim milk-Milk that has had the fat removed. The dry form of skim milk is known as nonfat dry milk.
- UHT milk is milk treated to pasteurization which involves heating milk to 138° to 150° C. (280° to 302° F.) for one or two seconds to enable a greater shelf-life and/or stability —Whey protein concentrate/isolate (WPC/WPI)—Whey protein concentrates are produced by ultrafiltration of whey. They can be in liquid or dry form and have a protein content typically ranging from 34 to less than 90%. When the protein concentration exceeds 90% the product is known as a whey protein isolate (WPI).

"Vegetable protein" means any protein isolated and/or extracted from a herbaceous plant with parts that are typically used as a source of food for mammals. Sources include, soy, pea, rice, hempseed, quinoa, various grains (i.e. wheat) and nut sources.

"Textured protein" means a by-product of extracting soybean oil that is often used as a meat analogue or meat extender.

"Droplet" means a subdivision of the feed being sprayed from the atomizer. As long as there is surface moisture in the spray, it is said to be composed of droplets.

"Particle" means a subdivision of the dried product. The shape of a particle depends on how the droplet was formed and how it behaved during drying.

"Aggregate" means an entity consisting of two or more particles adhering to each other.

"Aggregation" is the process whereby 2 or more particles adhere/are attracted to each other.

"Particle Size" means the size of a spherical particle expressed as there diameter measurement. For non-spherical particles, the size can be represented as an apparent diameter.

"Particle shape" means the process of atomizing and drying produces which in turn generates many particles that are non-spherical in shape. A "shape factor" is used to express the divergence of a particle shape from spherical.

"Size distribution" relates to the fact that droplets and particles that are produced in a spray dryer are never of one particular size. Any nozzle will produce both large and small droplets. The dryer must operate so that it is able to dry the largest droplet without scorching the smallest one. Size distributions can be represented by a cumulative distribution curve.

"Mean" or "median size" means a single value most suited to represent the entire distribution. Mean values can represent diameter, surface area, length, volume and other parameters.

"Hydrocolloid" means a colloid system where the colloid particles are hydrophilic polymer dispersed in water that is generally food grade. Examples include alginate, gelatin, carrageenan, pectin, citrus fibre, Beta-glucan, starch, guar gum, gum arabic, cellulose, fructooligosaccharide (FOS), galactooligosaccharides (GOS), and related derivatives (i.e. carboxymethylcellulose), arabinoxylans (i.e. citrus fibres) and mixtures thereof. A hydrocolloid is any food grade material, presented in a flowable powder format that can be dispersed and mixed with water.

BRIEF DESCRIPTION OF THE FIGURES

FIG. 3. List of divalent salt with potential use in the presented invention.

FIG. 4. Calibration range for the use of a weak acid and a relevant calcium salt (single sources or mixtures of relevant chloride, carbonate or citrate salts).

FIG. 14. Percent insoluble generated in the presence/absence of EDTA.

DETAILED DESCRIPTION OF THE INVENTION

Figure 1:
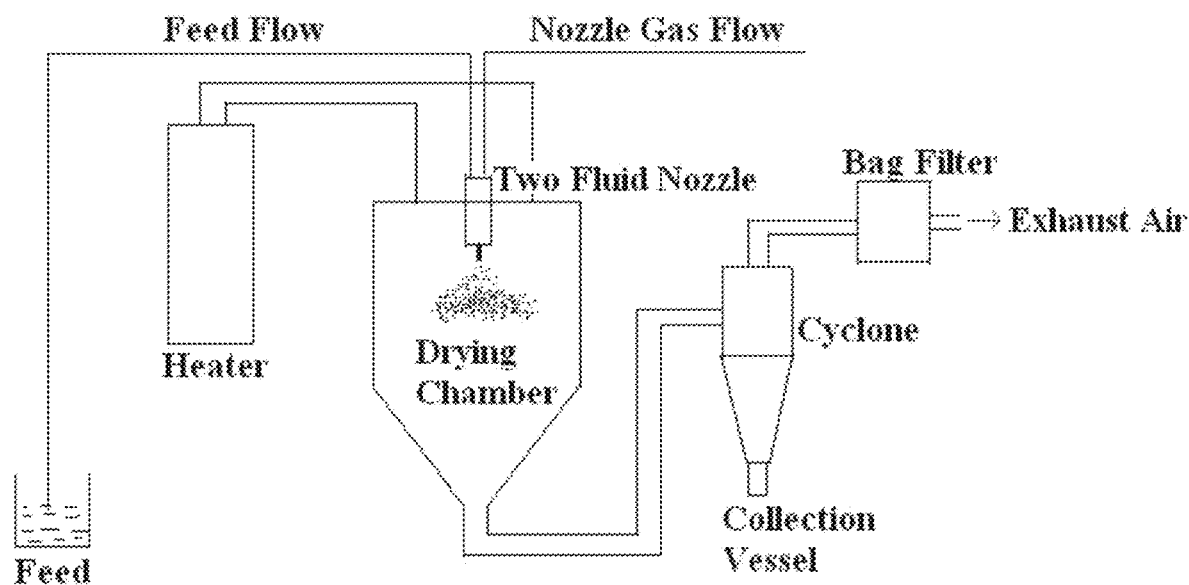
FIG. 1. Schematic of a standard Spray drier.
Figure 2:
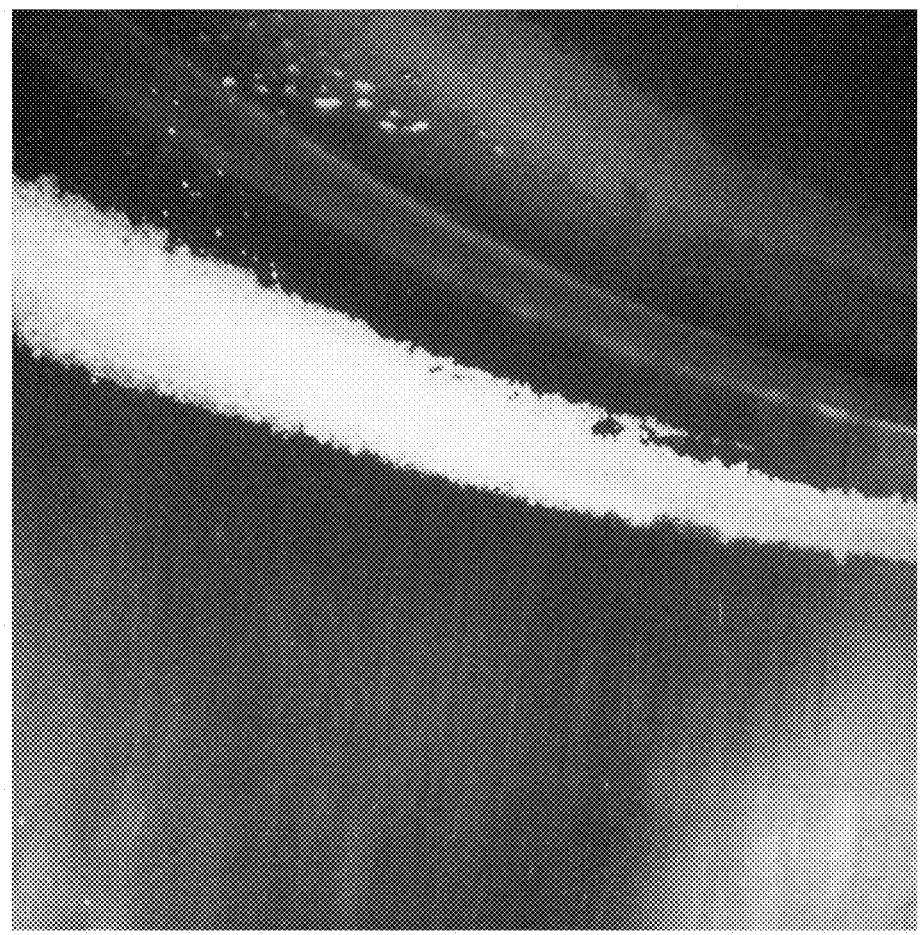
FIG. 2. Illustration of Mug Ring in a dry chamber.
Figure 5:
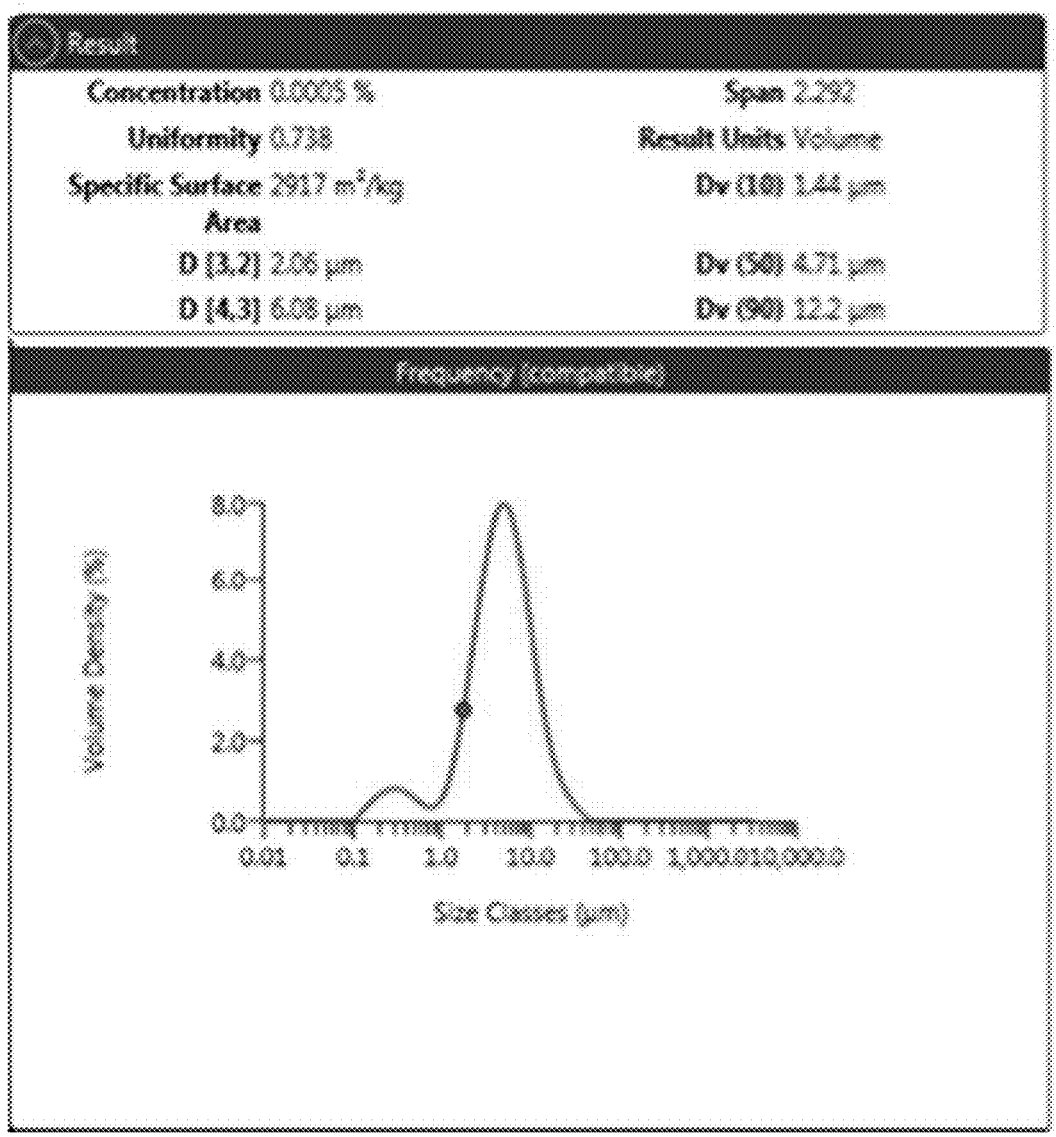
FIG. 5. Size distribution of spray-dried native protein (Skim Milk Protein) showing the small particle size (COMPARATIVE).

This invention relates to the making of microparticles in a spray dryer using a liquid feedstock comprising protein and a crosslinking agent in an inactive precursor form. The liquid feedstock comprises a crosslinking agent in the form of a volatile divalent metal salt, and a weak acid that maintains the pH of the feedstock prior to atomisation above the pH at which the volatile divalent metal salt solubilises. The feedstock typically dispersion remains dispersible, flowable to enable extrusion through a nozzle or rotating disk. Generally, no cross-linking or protein aggregation occurs before atomisation in the drying chamber due to sequential addition of native protein, a weak acid and a salt of a volatile base. The volatile divalent metal salt comprises a divalent metal cation (i.e. calcium, zinc, magnesium or potassium) capable of crosslinking and aggregating the protein, and a volatile anion (i.e. chloride, citrate, carbonate, sulfate, gluconate), that is sensitive to high heat. Thus, at relatively basic pH the salt is insoluble in the feedstock dispersion and unavailable to react with the native protein. However, upon heating of the atomised droplets in the drying chamber, four steps spontaneously occur: i) the heat of the drying chamber partially hydrolyses the protein; ii) the salt disassociates releasing and vaporising the volatile base i.e. anions; iii) evaporation of the volatile base reduces the pH of the dispersion; iv) the development of an acidic environment results in the solubilisation (bioavailability) of divalent metal cations iv) the bioavailability of divalent cations activates the crosslinking and subsequent aggregation reaction of partially hydrolysed protein. Without being bound by theory, the affinity of calcium ions for the protein is a higher attractive force relative the weak acid present. Hence the formation of a calcium ascorbate or calcium acetate is not a likely occurrence due to the high availability of protein aggregates and the significantly lower concentration of weak acid. Hence, the calcium will always be attracted and available for protein aggregation, crosslinking and polymerisation.

The release of the cross-linking agent, the generation of an acidic environment and the availability of partially hydrolysed protein, provides optimum conditions for the crosslinking and aggregation in the drying chamber of a standard spray-drier. Its activation of protein aggregation as a result of calcium availability is a consequence of protein-protein interaction via calcium (divalent cation). This results in disulfide bond formation during the spray drying. The use of a mixture of calcium salts sources i.e. calcium triphosphate, calcium chloride, calcium carbonate, can provide for a better and enhanced aggregation reaction. When two different protein sources are admixed prior to spray drying i.e. milk protein+pea protein or whey protein+sodium casein, the result is polymerisation of the proteins in the presence of divalent cations with the formation of ionic and disulfide links.

Thus, the present invention illustrates a crosslinking and agglomeration reaction between a protein and a divalent salt for the stabilisation of bioactive compounds with efficient atomisation characteristics for the generation of a flowable, stable, wettable and commercial powders suitable for a platform of food and therapeutic applications. In essence, the presented invention illustrates that the protein matrix material and crosslinking agent must be i) combined and introduced to the drying chamber as single liquid feedstock. The feedstock dispersion must remain soluble, flowable and suitable for extrusion through a nozzle or rotating disk. No cross-linking agglomeration reaction is should occur before atomisation in the drying chamber i.e. divalent ions must not be available for interaction. For this reason, a volatile base and weak acid are introduced sequentially into the feedstock in order to maintain a flowable dispersion. Upon introduction of the liquid feedstock into the dryer chamber, high heat conditions will catalyse the evaporation of the volatile base, leading to a significant pH reduction and concomitant release of (crosslinking) divalent cations, which will be present in a bioavailable, soluble form. The bioavailability of divalent cations will spontaneously activate the aggregation of protein molecules; the latter of which are hydrolysed as a result of high heat in the drying chamber. Hence, the release of cross-linking ions and the availability of partially hydrolysed protein, provides optimum conditions for a protein crosslinking and subsequent aggregation in the drying chamber.

Materials Required

Polymer:

Hydrocolloid or protein i.e. UHT milk, skim milk powder SMP, soy, milk or vegetable protein, FOS, GOS, carrageenan, alginate or hydrocolloid mixtures thereof Salt:

Divalent salt i.e. Calcium, Magnesium, zinc, or mixtures thereof

Acid

Weak Acid i.e. ascorbic acid, succinic acid, acetic acid, or mixtures thereof

Succinic Acid:

Succinic acid (IUPAC name is butanedioic acid is a diprotic, dicarboxylic acid with chemical formula $C_4H_6O_4$ and structural formula $HOOC-(CH_2)_2-COOH$. It is a white, odourless solid. Succinate plays a role in the citric acid cycle, an energy-yielding process. Succinic acid is used in the food and beverage industry, primarily as an acidity regulator. It is also sold as a food additive and dietary supplement, and is generally recognized as safe for those uses by the U.S. Food and Drug Administration. As an excipient in pharmaceutical products it is used to control acidity and, more rarely, in effervescent tablets. At the level succinic acid occurs naturally in foods, there is no evidence that it is hazardous to man or animals. Moreover, experimental animals tolerate succinic acid in amounts equivalent to several g per kg of body weight. By contrast, a reasonable average daily intake of succinic acid added to foods is estimated to be less than 0.01 mg per day, a dosage that is orders of magnitude less than that required to elicit toxic signs in experimental animals. Based on these considerations, the Select Committee concludes that: There is no evidence in the available information on succinic acid that demonstrates, or suggests reasonable ground to suspect, a hazard to the public when it is used at levels that are now current or that might reasonably be expected in the future. Ascorbic Acid: Ascorbic acid is a six carbon compound related to glucose. It is found naturally in citrus fruits and many vegetables. Ascorbic acid is an essential nutrient in human diets, and necessary to maintain connective tissue and bone. Its biologically active form, vitamin C, functions as a reducing agent and coenzyme in several metabolic pathways. Vitamin C is considered an antioxidant. It is a white to slightly yellow crystalline powder that gradually darkens on exposure to light. Solubility in water is approx. 80% at 100 Deg C. and 40% at 45 Deg C. Manufacture: The classical Reichstein-Grussner synthesis starts with reduction of D-glucose to D-sorbitol by hydrogenation over a nickel catalyst. The microbiological oxidation of D-sorbitol to L-sorbose is carried out with *Acetobacter xylinum*. On treatment of L-sorbose with acetone at low temperature in the presence of sulfuric acid, 2,3:4,6-di-O-isopropylidene-alpha-L-sorbofuranose formed. The di-O-isopropylidenyl protection of the hydroxyl-groups at C-2, C-3 and C-4, C-6 allows high-yield oxidation to di-O-isopropylidene-2-ketogulonic acid, without over-oxidation or other side reactions. The oxidation is carried out with potassium permanganate in alkaline solution. Treatment of/di-O-isopropylidene-2-ketogulonic acid/with hot water affords 2-keto-L-gulonic acid, which is converted to L-ascorbic acid by heating in water at 100 deg C. (20% yield) or by esterification and treatment with sodium methoxide in methanol followed by acidification with hydrogen chloride, yielding ca. 70% of/L-ascorbic acid/. The overall yield of ascorbic acid from D-glucose is 15-18%.

Analytical Method for Detection of Ascorbic Acid:

AOAC Method 967.21. Vitamin C (Ascorbic Acid) in Vitamin Preparations and Juices. 2,4-Dichloroindophenol Titrimetric Method. Ascorbic acid reduces oxidation-reduction indicator dye, 2,4-dichloroindophenol, to colorless solution. At end point, excess unreduced dye is rose pink in acid solution. Vitamin is extracted and titration is performed in presence of HPO3-HOAc or HPO3-HOAc—H2SO4 solution to maintain proper acidity for reaction and to avoid autoxidation of ascorbic acid at high pH. (Reference: Association of Official Analytical Chemists. Official Methods of Analysis. 15th ed. and Supplements. Washington, D.C.: Association of Analytical Chemists, 1990, p. 1059).

General Methodology

Spray drying of an aqueous dispersion containing a hydrocolloid mixture containing sufficient protein to allow a crosslinking and subsequent aggregation reaction (UHT milk, skim milk powder, vegetable protein, or mixtures thereof).
- A divalent salt (Calcium, Magnesium, zinc) is introduced that is soluble at acidic pH only.
- A weak acid (ascorbic acid, succinic acid or acetic acid) is introduced at a pH (preferably above pH 5, ideally above pH 7) just above the pike with a volatile base (calcium carbonate, calcium chloride, etc.; See FIG. 4).
- Under these conditions, the divalent salt is insoluble and ions are not available for cross-linking and aggregation with the protein molecules from the hydrocolloid component of the mixture.
- when a hydrocolloid such as FOS or GOS is employed, the hydrocolloid can be admixed to the weak acid, or added to the liquid feedstock at any point but typically just prior to the preheating stage.
- The solution (liquid feedstock) in this fluid state is preheated and pumped through the nozzle of the single/multi-stage spray drier, where it is effectively atomised.
- Inlet and outlet temperatures are maintained in accordance with standard commercially viable conditions to allow appropriate atomisation. i.e. 180 DegC inlet and 85-90 Dec outlet temperature
- Upon atomisation at these temperatures the volatile base is vaporised and the protein content enters into a hydrolysed state.
- Upon evaporation of the base, the pH is reduced (hydrogen ions are released into solution) and divalent ions are released and enter a bioavailable state.
- Calcium/the relevant divalent cations is readily available for crosslinking and aggregation with the protein/hydrocolloid source, mixture thereof.
- The crosslinking and subsequent aggregation reaction is initiated as a result of the temperature of the drier. i.e. high temperature permits evaporation of the volatile base, and concomitant hydrolysis of the protein source and bioavailability of the divalent cations. These three conditions accelerate the cross-linking aggregation and entrapment of an active compound.
- Spray drying is the method of choice as it the industry standard for dehydration of materials. Furthermore, it prevents multiplication of contaminants because powders are easy to handle in the field and the method is well documented an accepted across all industrial disciplines.

Method 1:

- Whey protein isolate (WPI) or concentrate (WPC) at a total protein content of 8.0% w/v (protein basis) in water
- The protein dispersion is centrifuged at 10,000 rpm; 16 Dig Celsius; 45 minutes
- Supernatant is agitated overnight at 4° C. at pH 7.5
- The protein dispersion is filtered (0.2 micron) at room temperature
- A solution (8.0% w/v) of ascorbic acid is prepared in water and agitated at room temperature before addition of 2% FOS
- A calcium β-hydroxy-β-methylbutyrate (CaHMB) solution (0.4% (w/v) is prepared and dispersed in water.
- The pH is adjusted to 7.5 using 4M NaOH. This represents a Asc/CaHMB mix.

The pellet of cells/powdered bioactive material is resuspended in the protein dispersion Cell concentrations is approx. $1 \times 10^{11}$ CFU/mL.

Bioactive material can be dispersed at max 50% solid content.

The protein dispersion with cells/active is then mixed with Ascorbic-Calcium solution at ratio 1:1 (v/v)

Agitation is then performed at 65° C. to pre-heat for the drier

At this point the solution is fluid and call the feedstock

Spray dry the suspension using a single-stage drier

Standard inlet and outlet temperatures will apply i.e. inlet 180° C. and outlet 85-90° C.

Delivery of suspension via peristaltic pump was fixed to 600 mL/hr (Bench top) or 20 L per hour (pilot scale).

Nozzle atomization is utilized as per standard industry practice.

Material is dried to a Aw of 0.2 and storage at refrigerated temperatures in hermetically sealed drums/foil bags.

Method 2

Pea protein isolate (PPI) prepared at a total protein content of 9.0% w/v (protein basis) in water The protein dispersion is centrifuged at 10,000 rpm; 16 Dig Celsius; 45 minutes Supernatant is agitated overnight at 4° C. at pH 7.2

The protein dispersion is filtered (0.2 micron) at room temperature

A solution (12.0% w/v) of ascorbic acid is prepared in water and agitated at room temperature before addition of 2% FOS (w/v)

A calcium carbonate (or calcium ascorbate or calcium citrate or CaHMB) (0.4% (w/v) is prepared and dispersed in water.

Ascorbic acid and Calcium source is admixed

At this point, ascorbic acid concentrations are optimum to permit the natural and adequate neutral pH for the feedstock i.e. neutral pH to avoid maintain divalent ions in an 'Unavailable state".

This represents a Asc/Ca mix.

The pellet of cells/powdered bioactive material is resuspended in the protein dispersion Cell concentrations is approx. $1\times10^{11}$ CFU/mL.

Bioactive material can also be dispersed at max 50% solid content.

The protein dispersion with cells/active is then mixed with Ascorbic-Calcium dispersion at ratio 1:1 (v/v)

Agitation is then performed at 65° C. to pre-heat for the drier

At this point the solution is fluid and classified as feedstock

Spray dry the suspension using a single stage drier

Standard inlet and outlet temperatures will apply i.e. inlet 180° C. and outlet 85-90° C.

Delivery of suspension via peristaltic pump was fixed to 600 mL/hr (Bench top) or 20 L per hour (pilot scale).

Nozzle atomization was used as per standard industry procedure.

Material is dried to a Aw of 0.2 and storage at refrigerated temperatures in hermetically sealed drums/foil bags.

Method 3

Pea protein isolate (PPI) or milk protein isolate (WPI) prepared at a total protein content of 9.5% w/v (protein basis) in water The protein dispersion is centrifuged at 10,000 rpm; 16° C.; 45 minutes Supernatant is agitated overnight at 4° C. at pH 7.5

The protein dispersion is filtered (0.2 micron) at room temperature

A solution (12.0% w/v) of ascorbic acid is prepared in water and agitated at room temperature before addition of 2% FOS (w/v)

A calcium triphosphate, calcium chloride, calcium carbonate solution totally (1.8% (w/v) is prepared and dispersed in water.

Ascorbic acid and Calcium mix is admixed

At this point, ascorbic acid concentrations are optimum to permit the natural and adequate neutral pH for the feedstock i.e. neutral pH to avoid maintain divalent ions in an 'Unavailable state".

This represents a Asc/Ca mix.

The pellet of cells/powdered bioactive material is resuspended in the protein dispersion Cell concentrations is approx. $1\times10^{11}$ CFU/mL.

Bioactive material can also be dispersed at max 50% solid content.

The protein dispersion with cells/active is then mixed with Ascorbic-Calcium dispersion at ratio 1:1 (v/v)

Agitation is then performed at 65° C. to pre-heat for the drier

At this point the solution is fluid and classified as feedstock

Spray dry the suspension using a single stage drier

Standard inlet and outlet temperatures will apply i.e. inlet 180° C. and outlet 85-90° C.

Delivery of suspension via peristaltic pump was fixed to 600 mL/hr (Bench top) or 20 L per hour (pilot scale).

Nozzle atomization was used as per standard industry procedure.

Material is dried to a Aw of 0.2 and storage at refrigerated temperatures in hermetically sealed drums/foil bags.

Method 4

Whey Protein (WPI/WPC) and pea protein isolate (PPI) prepared at a total protein content of 15.0% w/v (protein basis) in water The protein dispersion is centrifuged at 10,000 rpm; 16° C.; 45 minutes Supernatant is agitated overnight at 4° C. at pH 7.2

The protein dispersion is filtered (0.2 micron) at room temperature

A solution (12.0% w/v) of succinic acid is prepared in water and agitated at room temperature A calcium triphosphate (0.5% (w/v) is prepared and dispersed in water.

Succinic acid and Calcium source is admixed

At this point, succinic acid concentrations are optimum to permit the natural and adequate neutral pH for the feedstock i.e. neutral pH to avoid maintain divalent ions in an 'Unavailable state".

This represents a Succ/Ca mix.

The pellet of cells/powdered bioactive material is resuspended in the protein dispersion Cell concentrations is approx. $1\times10^{11}$ CFU/mL.

Bioactive material can also be dispersed at max 50% solid content.

The protein dispersion with cells/active is then mixed with Ascorbic-Calcium dispersion at ratio 1:1 (v/v)

Agitation is then performed at 65° C. to pre-heat for the drier

At this point the solution is fluid and classified as feedstock

Spray dry the suspension using a single stage drier

Standard inlet and outlet temperatures will apply i.e. inlet 180° C. and outlet 85-90° C.

Figure 6:
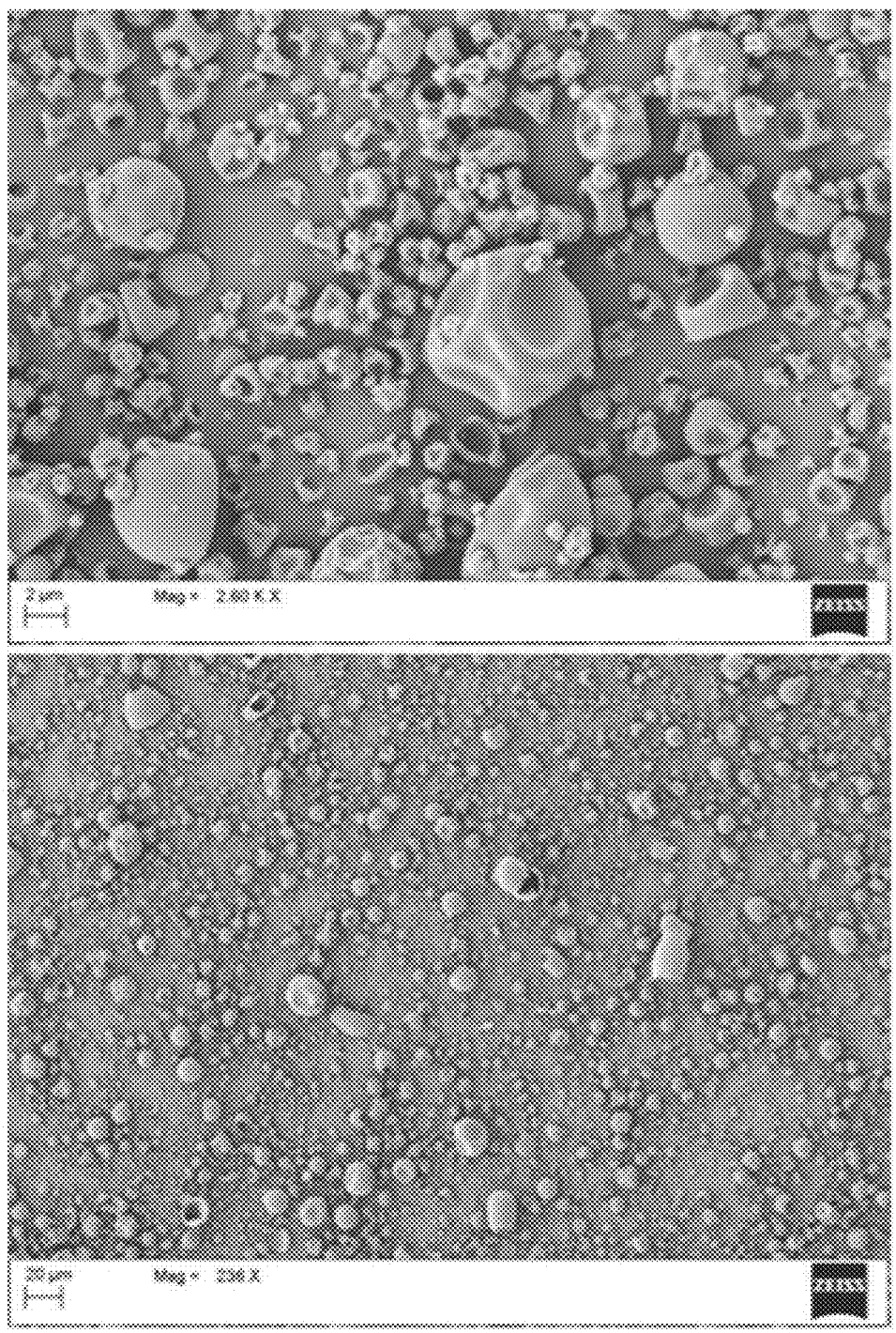
FIG. 6. SEM image of native protein (Skim Milk Protein) spray-dried in the absence of the Acid/base mix (COMPARATIVE).

Delivery of suspension via peristaltic pump was fixed to 600 mL/hr (Bench top) or 20 L per hour (pilot scale).
Nozzle atomization was used as per standard industry procedure.
Material is dried to a Aw of 0.2 and storage at refrigerated temperatures in hermetically sealed drums/foil bags
Method 5:
Whey Protein (WPI/WPC) and pea protein isolate (PPI) prepared at a total protein content of 15.0% w/v (protein basis) in water
The protein dispersion is centrifuged at 10,000 rpm; 16° C.; 45 minutes
Supernatant is agitated overnight at 4° C. at pH 7.2
The protein dispersion is filtered (0.2 micron) at room temperature
A solution (12.0% w/v) of ascorbic acid is prepared in water and agitated at room temperature
A calcium triphosphate, calcium chloride, calcium carbonate solution totally (1.8% (w/v) is prepared and dispersed in water.
Ascorbic acid and Calcium mix is admixed
At this point, ascorbic acid concentrations are optimum to permit the natural and adequate neutral pH for the feedstock i.e. neutral pH to avoid maintain divalent ions in an 'Unavailable state".
This represents a Asc/Ca mix.
The pellet of cells/powdered bioactive material is resuspended in the protein dispersion
Cell concentrations is approx. $1\times10^{11}$ CFU/mL.
Bioactive material can also be dispersed at max 50% solid content.
The protein dispersion with cells/active is then mixed with Ascorbic-Calcium dispersion at ratio 1:1 (v/v)
Agitation is then performed at 65° C. to pre-heat for the drier
At this point the solution is fluid and classified as feedstock
Spray dry the suspension using a single stage drier
Standard inlet and outlet temperatures will apply i.e. inlet 180° C. and outlet 85-90° C.
Delivery of suspension via peristaltic pump was fixed to 600 mL/hr (Bench top) or 20 L per hour (pilot scale).
Nozzle atomization was used as per standard industry procedure.
Material is dried to a Aw of 0.2 and storage at refrigerated temperatures in hermetically sealed drums/foil bags
Method 6: Generation of Stable Bioactive Vitamin C
Whey Protein (WPI/WPC) and pea protein isolate (PPI) prepared at a total protein content of 2.0% w/v (protein basis) in water
The protein dispersion is centrifuged at 10,000 rpm; 16° C.; 45 minutes
Supernatant is agitated overnight at 4° C. at pH 7.2
A solution (3.5.0% w/v) of citrus fibre is prepared in water and agitated at room temperature
Fructo-oligosaccahride (FOS) is prepared at 2.0% (W/v) concentration
The protein and fibre dispersions are filtered (0.2 micron) at room temperature
Protein, FOS and citrus fibre is admixed.
A solution (82.0% w/v) of ascorbic acid is prepared in water and agitated at room temperature
A calcium triphosphate or calcium chloride solution total 1.8% (w/v) is prepared and dispersed in water.
Ascorbic Acid and Calcium Mix is Admixed
At this point, ascorbic acid concentrations are optimum to permit the natural and adequate neutral pH for the feedstock i.e. neutral pH to avoid maintain divalent ions in an 'Unavailable state".
The protein, FOS, fibre suspension is then mixed with Ascorbic-Calcium dispersion at ratio 1:1 (v/v)
Agitation is then performed at 65 Degrees Celsius to pre-heat for the drier
At this point the solution is fluid and classified as feedstock
Spray dry the suspension using a single stage drier
Standard inlet and outlet temperatures will apply i.e. inlet 180 Dec and outlet 85-90 DEgC
Delivery of suspension via peristaltic pump was fixed to 600 mL/hr (Bench top) or 20 L per hour (pilot scale)
Nozzle atomization was used as per standard industry pro
Results:
Sequential Formulation:

Formulation optimisation of a weak acid and the salt of a volatile base system where the salt is insoluble at neutral pH values. Ascorbic acid and calcium carbonate were screened at various concentration as illustrated in FIG. 4. Aliquots of 0.2M of the calcium salt was added to ascorbic acid to determine the appropriate concentration to make an feasible mix for drying.

It is evident that a minimum quantity of calcium is required to react with the protein content present in the mix. It is also evident that a minimum quantity of weak acid (ascorbic acid is required) to raise the pH to the relevant level above the pKa of the calcium carbonate. Prior to spray drying the optimum ascorbic/succinic acid concentrations of 0.2 M-2.2 M worked well for introduction to calcium carbonate in the range of 0.1 M-2.0 M. Outside these ranges the mixture becomes turbid and there are precise ratios that are required to maintain the appropriate neutral pH, while also having adequate calcium available for crosslinking and aggregation. When the proposed formulation were applied to a spray-drier, the particle size is again significantly change as a result of the hydrolysis of the protein source with concomitant cross-linking and aggregation reaction with the available calcium ions.

When resultant powders were assessed under Light Microscope, the following changes were observed in contrast to the raw materials. They physiochemical properties of the suspension and related dry powder illustrate the occurrence of the cross-linking reaction between the partially hydrolysed protein and the solubilised $Ca^{2+}$ ions. The pH of the suspension in a stepwise manner is illustrated as follows:

| | |
|---|---|
| Initial weak Acid/Calcium Salt Mix | pH 4.1-5.0 |
| Protein hydrocolloid suspension + Mix (T0) | pH 7.0-.7.5 |
| After Spray Drying | pH 4.5-5.0 |

Determination of Size Distribution

The presented invention was tested in a standard spray drying process and the effect of the feedstock formulation (protein+weak acid+salt of a volatile base) was investigated as a function of particle size. Firstly, it was important to investigate the effect of spray drying the protein only in the absence of the acid base mixture and FIG. 5 illustrates the size distribution a native protein source, after a spray drying process. The size distribution is relatively low i.e. 12.2 microns±1.53 microns with a narrow size distribution. This illustrates the expected size range that a native protein would generate after heat processing through a spray drier. Microscopy illustrated no change in the particle size of native protein (FIG. 6) where the average particle size is expected to be 12.5 microns.

Figure 7:
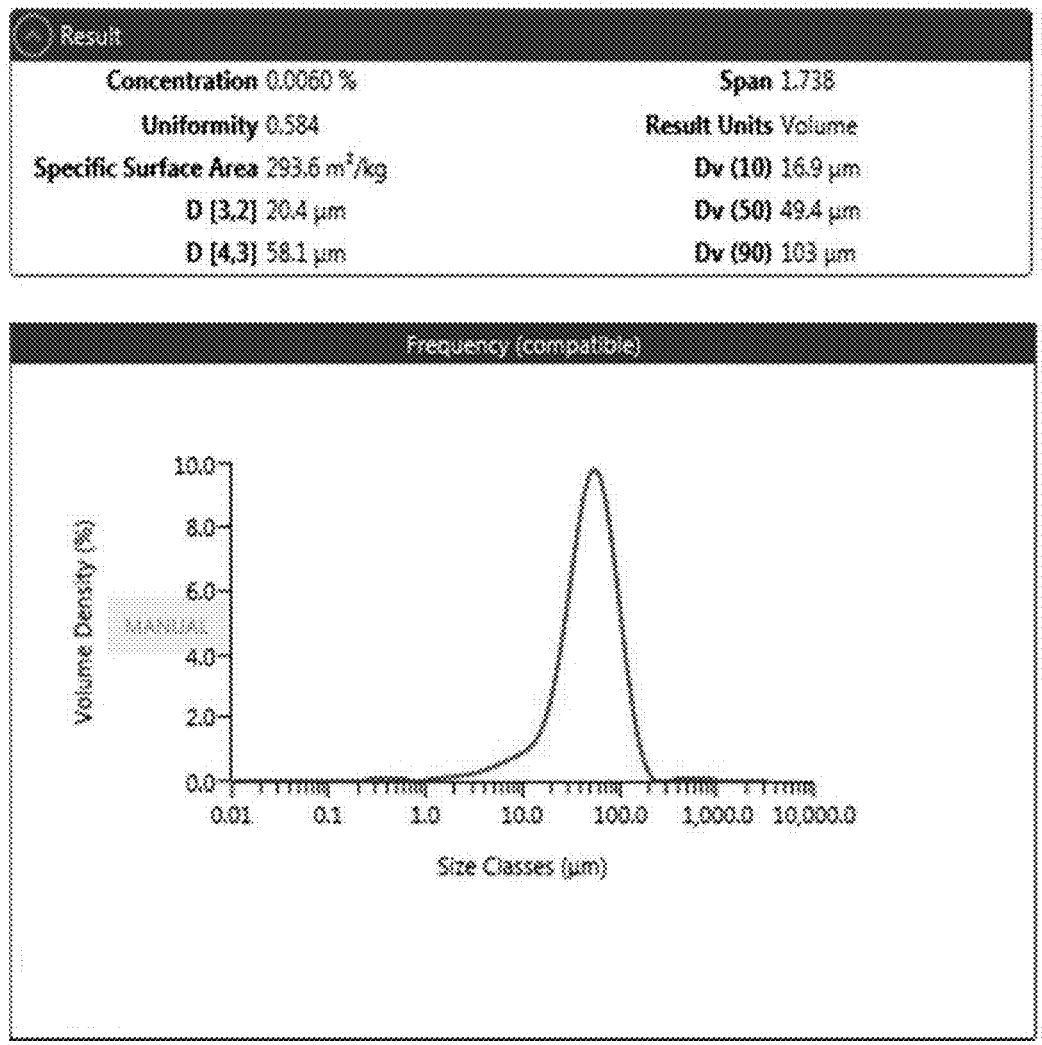
FIG. 7. Size distribution of pea protein microparticles spray-dried according to the method of the invention in the presence of a calcium salt mixture (3 different calcium salt sources).
Figure 8:
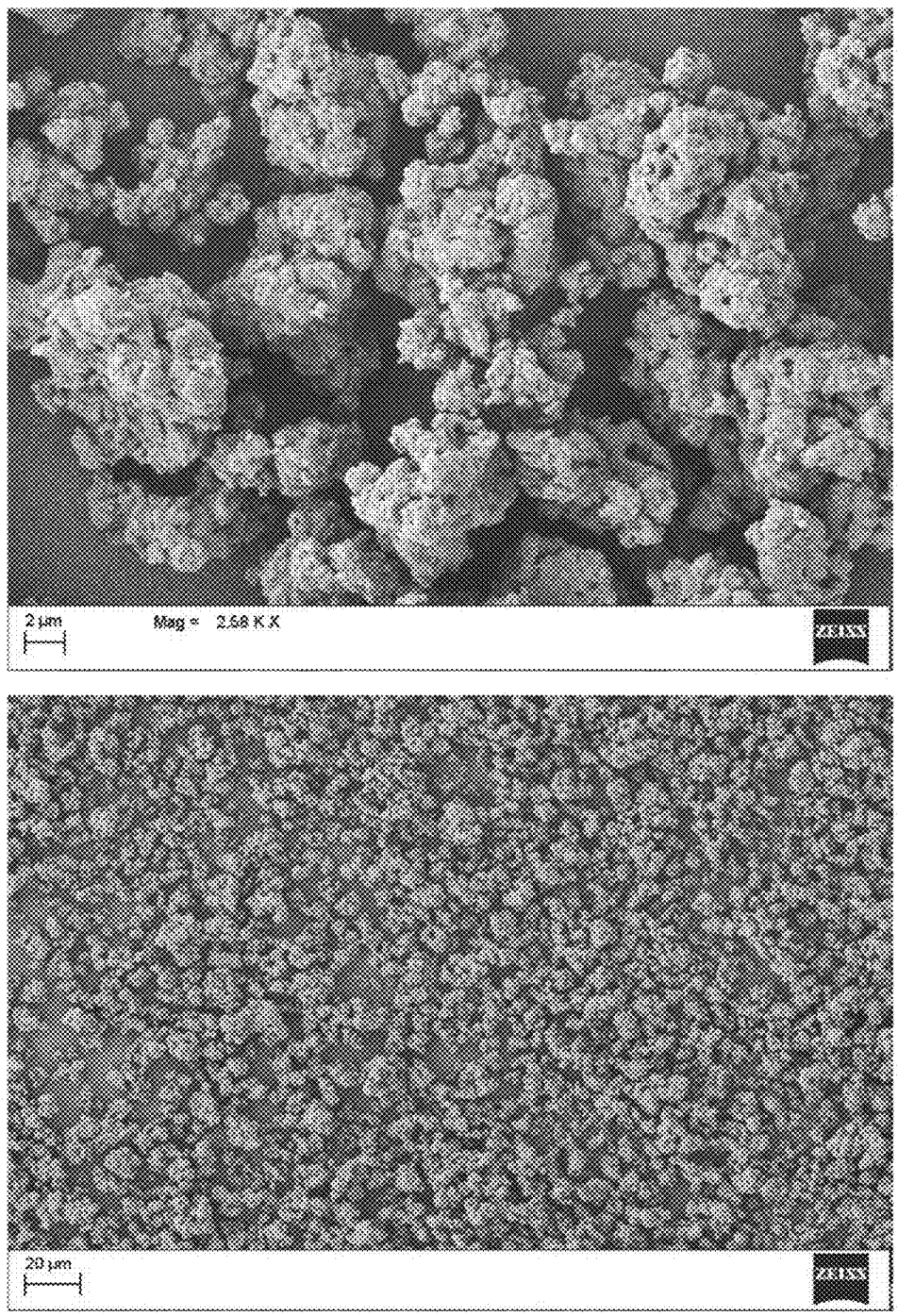
FIG. 8. SEM images illustrating the pea protein microparticles of the invention of FIG. 7.

FIG. 7 illustrates the size distribution of the mix when the calcium is sourced from several salts i.e. chloride, carbonate, phosphate. The size distribution is significantly greater than native protein after drying; which endorses the aggregation of protein particles, as evidenced in FIG. 6. Scanning Electron Microscope images illustrate a change in particle morphology as a result of drying in the presence of a calcium salt mixture. In FIG. 8 the presence is aggregated protein is shown with a large particle size. Individual aggregated particulates are 103 microns±1.5 microns with a narrow distribution for individual protein particles. This illustrates a stable drying process and efficient atomisation process.

Figure 9:
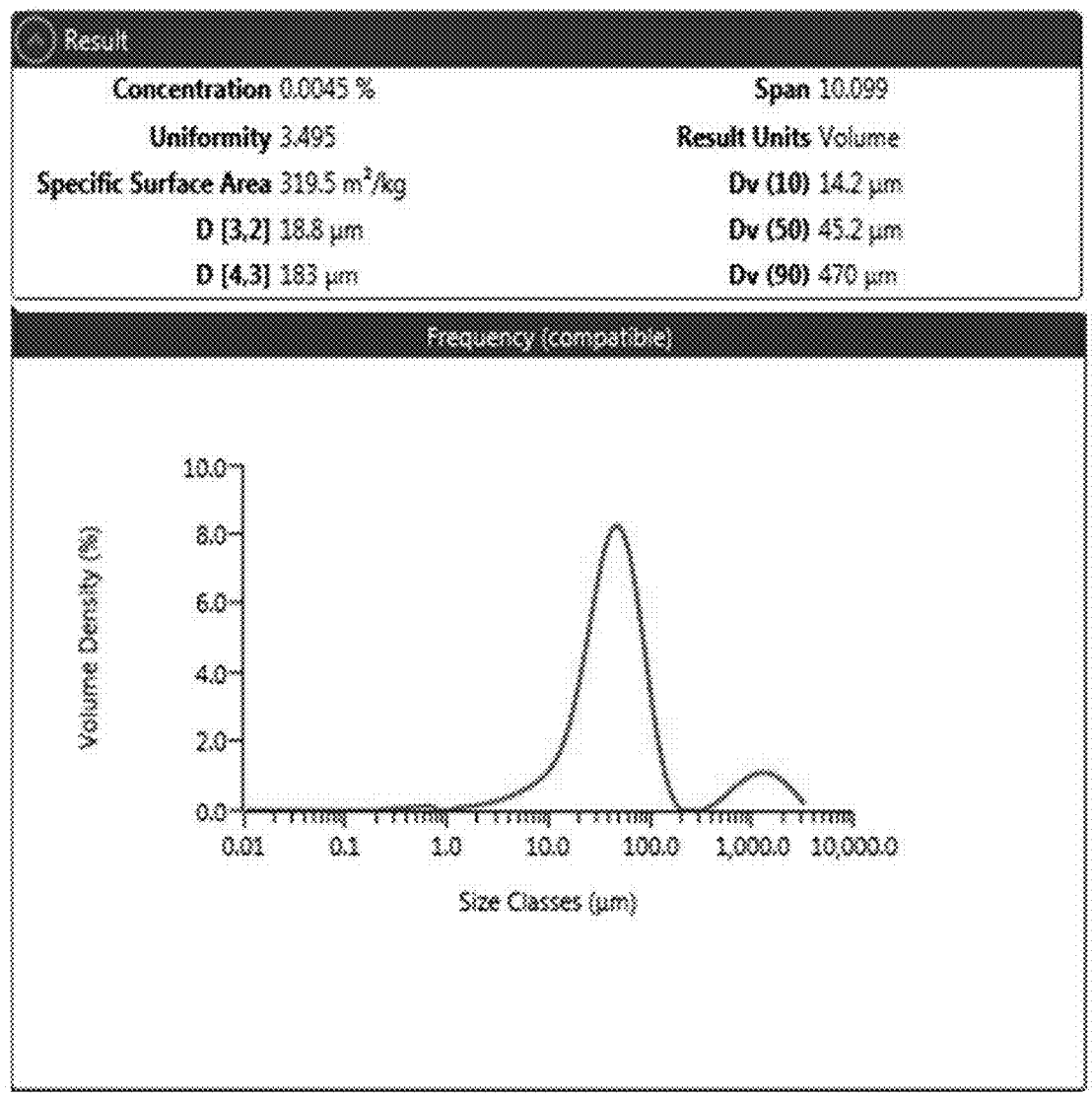
FIG. 9. Size distribution of microparticles spray dried according to the invention, and which employ two protein sources (Whey Protein Isolate and Pea Protein isolate) and one calcium salt (calcium triphosphate).
Figure 10:
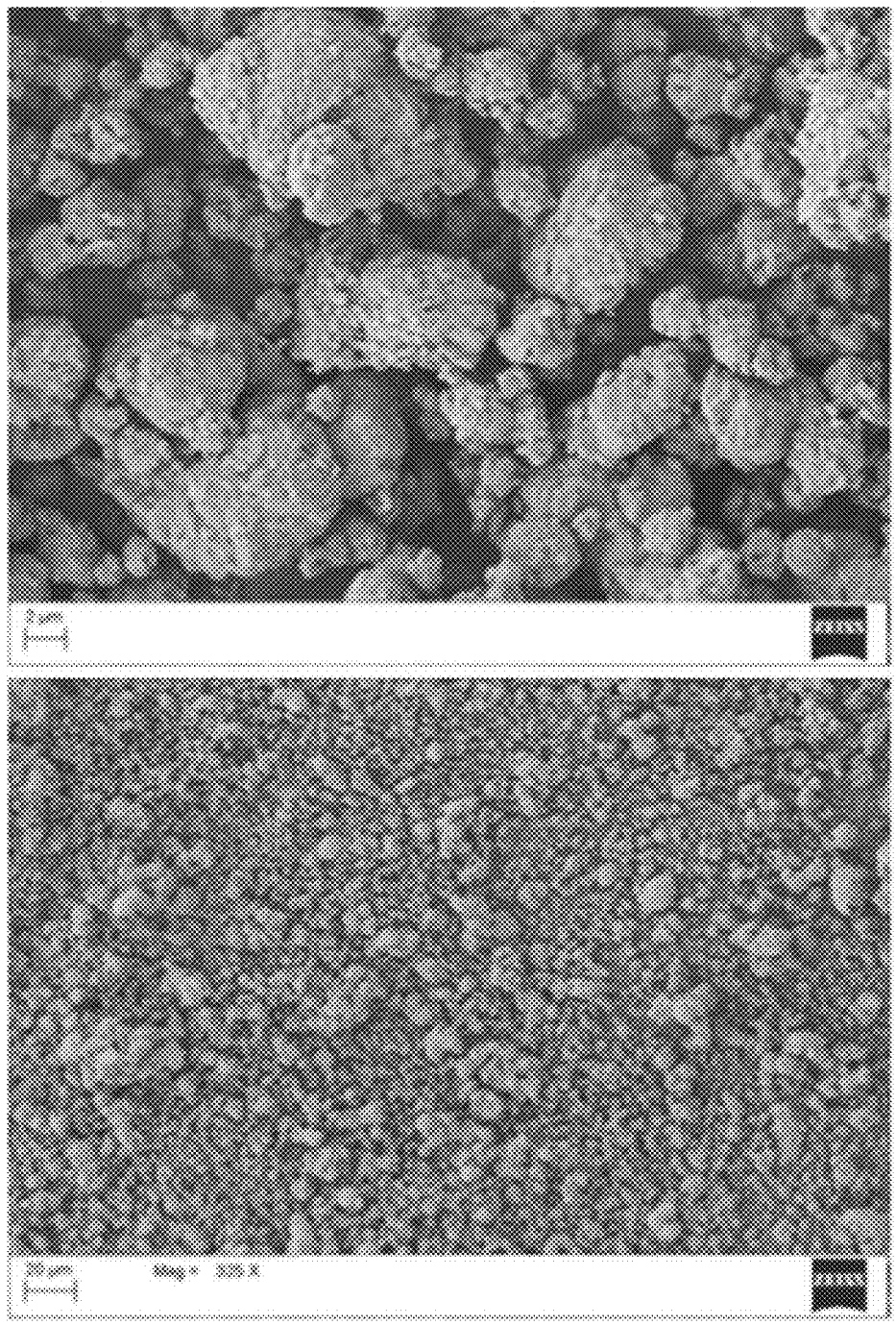
FIG. 10. SEM image illustrating the pea protein/WPI microparticles of the invention of FIG. 9.
Figure 11:
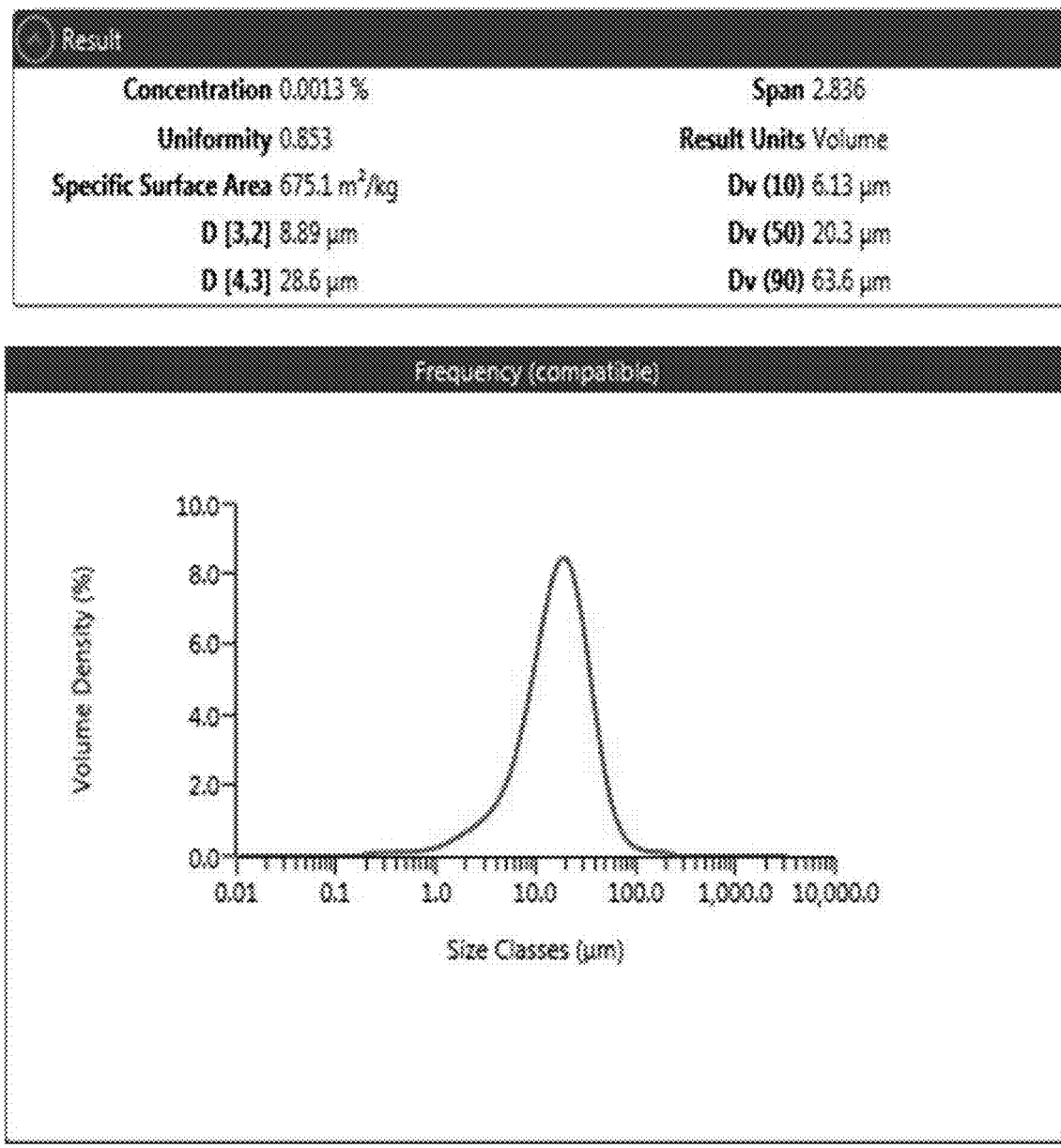
FIG. 11. Size distribution of microparticles spray dried according to the invention, and which employ one protein source (Whey Protein Isolate) and one calcium salt (calcium carbonate).

The use of two protein sources and once calcium source further illustrates the aggregation process (FIGS. 9 and 10) with the generation of aggregates with diameters of approx. 56.34 microns. SEM endorses the completion of the protein aggregation reaction. Most importantly the use of i) one/two protein sources and ii) a single/cocktail of calcium salt source will dictate the final particle size of the dried powder. This final particle size will be further dictate the production application for the ingredient. FIGS. 10 and 11 further illustrate the aggregation reaction when one protein and one calcium salt is utilised. Particles are generated with a narrow size distribution i.e. 63.6 microns±1.9 microns with specific product applications.

The particle remain below 10 microns in diameter which further provides for a stable dispersion of the powder in aqueous solutions. In essence, the particles a stable dispersion of soluble aggregates for the protection of a specific entrapped bioactive.

Figure 12:
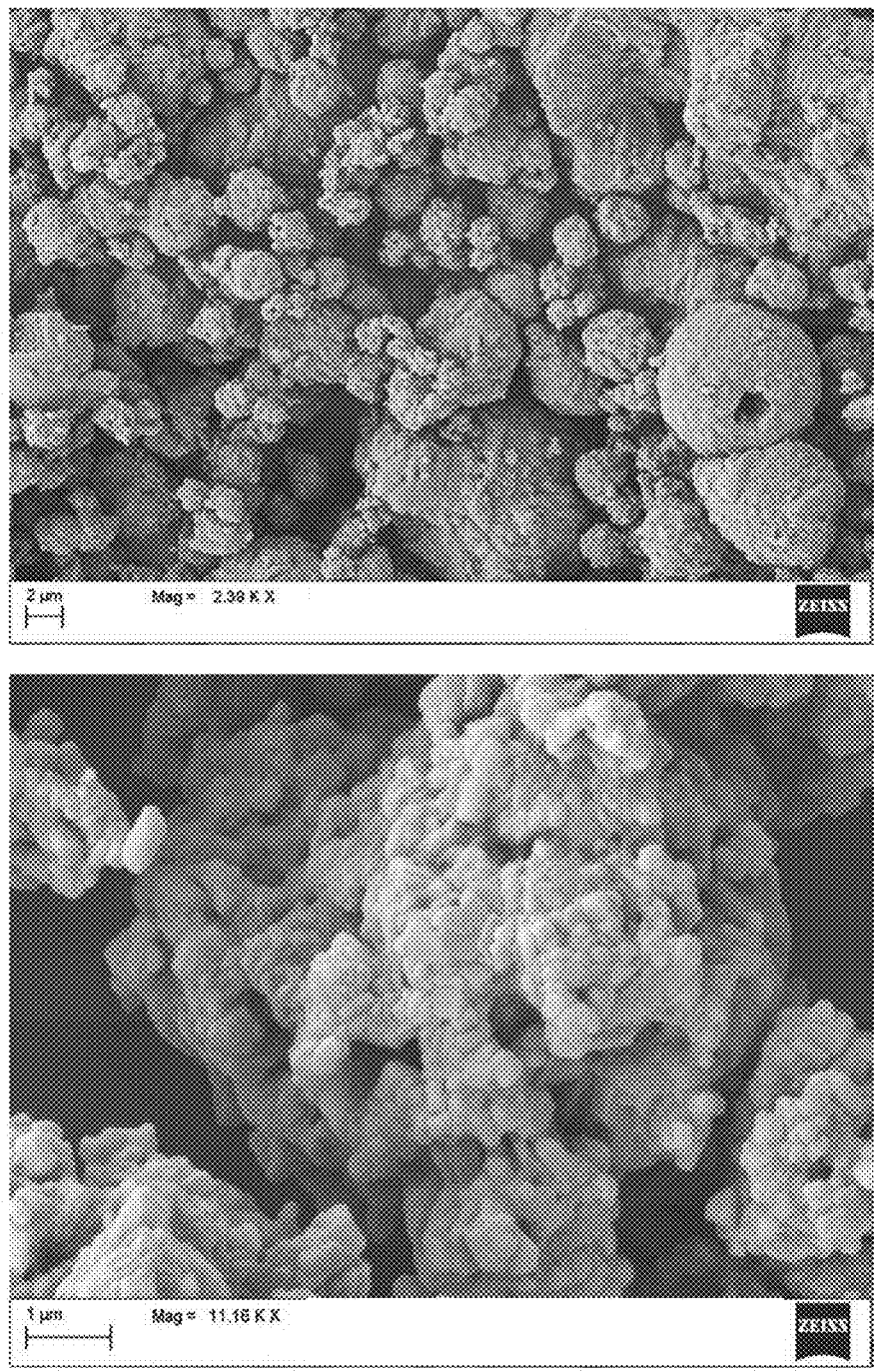
FIG. 12. SEM image illustrating the WPI microparticles of the invention of FIG. 11.

The type of weak acid utilised has no significant impact upon the survival of specific bioactives. FIG. 12 illustrates that the use of succinic acid or ascorbic acid has not effect on the viability of probiotic bacteria during the drying process. The pH of the final product will dictate the type of weak acid to be utilised.

Figure 13:
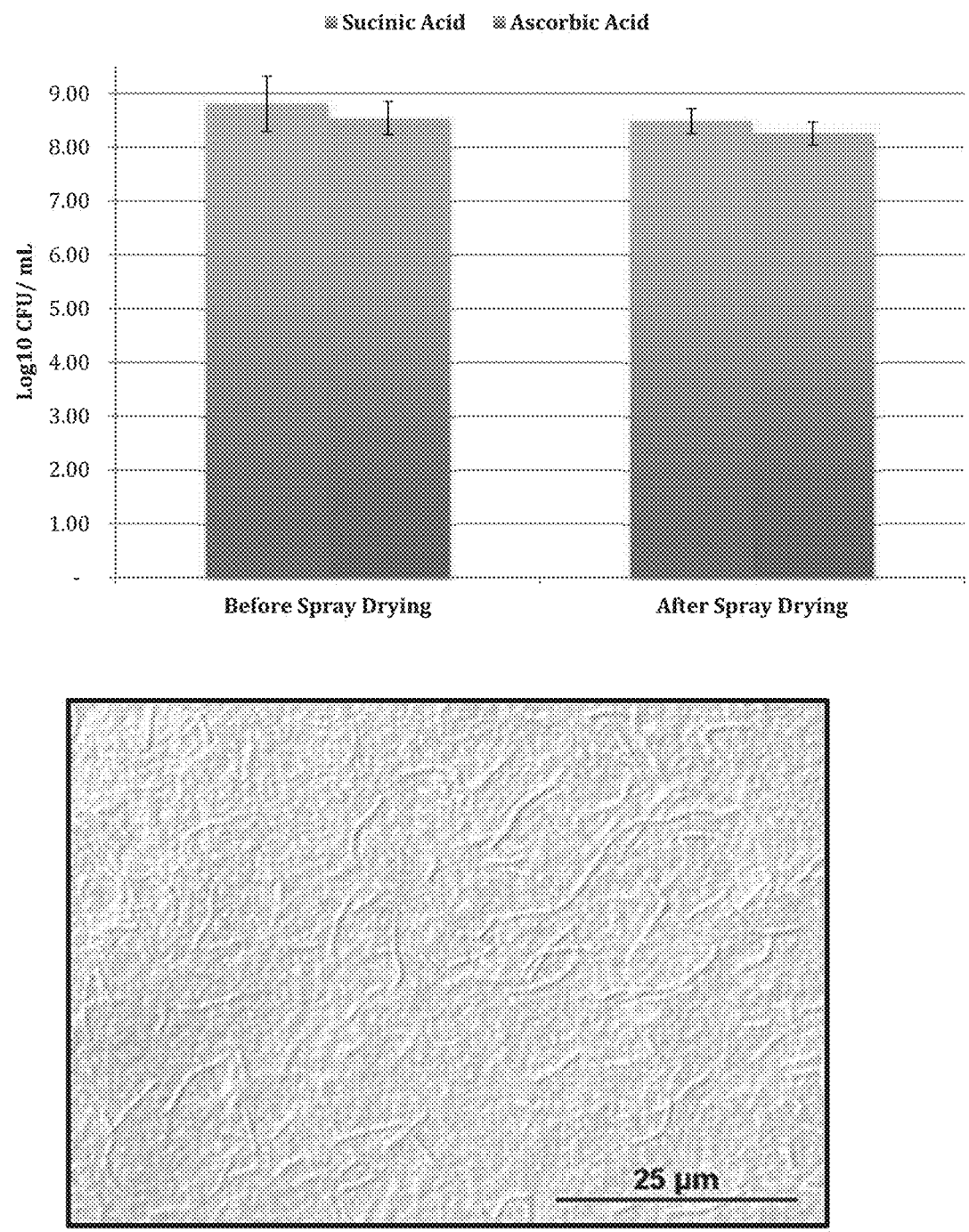
FIG. 13. Survival of a probiotic stain (*Lb. acidophilus*) in the presence of succinic acid and ascorbic acid as the weak acid in the mix. Image of the particulate network after drying with entrapped probiotic cells.

The use of calcium as a crosslinking/aggregation agent is further endorsed in FIG. 13 where EDTA is utilised to bind the protein and sedimentation reactions are also performed. EDTA was utilised in this experiment in order to verify if the calcium was in a bound or free state. The assay was performed as follows:

Calcium Carbonate was admixed with EDTA in a 2:1 ratio to ensure the excess of EDTA in the reaction mixture
Adjust the pH to 8.5 and 10 in order to accelerate the binding capacity of EDTA
Several treatment were prepared as outlined in Table 2
All samples were Incubated for 24 h at room temperature
Following incubation, pH values were recorded
All samples were sedimentation of insolubles were measured
Insoluble matter was calculated on a percent basis It is evident that the spray dried powder with the full reaction mixture generated a higher pelleted material relative the pre-dried mixture. This endorses the fact that the drying process stimulates the aggregation of proteins, which is demonstrated via the presence of higher pellet percent after sedimentation tests i.e. before spray drying the mixture illustrates 9.83% aggregated material; while after spray-drying of the mixture 22.8% sedimentation is generated.

The invention claimed is:

1. A method of producing microparticles by spray drying, the method comprising the steps of:
providing a food-grade spray-drying feedstock solution comprising water, a volatile divalent metal salt, a weak acid, 5-15% dairy or vegetable protein (w/v) and an active agent, the feedstock solution having a pH at which the volatile divalent metal salt is substantially insoluble;
spray drying the feedstock solution at an elevated temperature to provide atomised droplets whereby the volatile divalent metal salt disassociates at the elevated temperature to release divalent metal ions which crosslink and aggregate the protein in the atomised droplets to produce microparticles having a crosslinked aggregated protein matrix and the active agent dispersed throughout the matrix, wherein the active agent is a cellular active agent, the spray-drying feedstock comprises 1-20% of the active agent (w/v), and the solids content of the feedstock is 40-70%.

2. The method according to claim 1 in which the spray-drying feedstock comprises 1-10% hydrocolloid (w/v).

3. The method according to claim 1 in which the spray-drying feedstock comprises 1-3% hydrocolloid (w/v).

4. The method according to claim 2 in which the hydrocolloid is selected from the group consisting of fructooligosaccharide, galactooligosaccharide, carrageenan and guar gum.

5. The method according to claim 4 in which the spray-drying feedstock comprises 1-3% fructooligosaccharide (w/v).

6. The method according to claim 1 in which the volatile divalent metal salt is selected from the group consisting of a divalent metal ion carbonate, a divalent metal ion chloride, a divalent metal ion phosphate, a divalent metal ion citrate, a divalent metal ion ascorbate, a divalent metal ion HMB, and a mixture thereof.

7. The method according to claim 1 in which the weak acid is ascorbic acid or succinic acid or a mixture thereof.

8. The method as claimed in claim 1 in which the protein is a dairy protein selected from the group consisting of UHT milk, milk protein, skim milk powder, and a mixture thereof.

9. The method as claimed in claim 1 in which the protein is a vegetable protein selected from the group consisting of pea protein, rice protein, wheat protein, and a mixture thereof.

10. A preparation of spray-dried microparticles prepared according to the method of claim 1.

11. A method of producing microparticles by spray drying, the method comprising the steps of:
providing a food-grade spray-drying feedstock solution comprising water, a volatile divalent metal salt, a weak acid, 5-15% dairy or vegetable protein (w/v), and an active agent, the feedstock solution having a pH at which the volatile divalent metal salt is substantially insoluble;
spray drying the feedstock solution at an elevated temperature to provide atomised droplets whereby the volatile divalent metal salt disassociates at the elevated temperature to release divalent metal ions which crosslink and aggregate the protein in the atomised droplets to produce microparticles having a crosslinked aggregated protein matrix and the active agent dispersed throughout the matrix, wherein the active agent is a compound and the spray-drying feedstock comprises 30-60% of the active agent (w/v).

12. The method according to claim 11 in which the solids content of the feedstock is 50-80%.

13. A method of producing microparticles by spray drying, the method comprising the steps of:

providing a food-grade spray-drying feedstock solution comprising water, a volatile divalent metal salt, a weak acid, 5-15% dairy or vegetable protein (w/v), and an active agent, the feedstock solution having a pH at which the volatile divalent metal salt is substantially insoluble;

spray drying the feedstock solution at an elevated temperature to provide atomised droplets whereby the volatile divalent metal salt disassociates at the elevated temperature to release divalent metal ions which crosslink and aggregate the protein in the atomised droplets to produce microparticles having a crosslinked aggregated protein matrix and the active agent dispersed throughout the matrix, wherein the spray-drying feedstock solution is prepared by the steps of:

preparing an aqueous solution of the weak acid;

preparing an aqueous dispersion of the volatile divalent metal salt;

mixing the aqueous solution and the aqueous dispersion to provide a weak acid/volatile divalent metal salt dispersion and adjusting the pH such that the volatile divalent metal salt is substantially insoluble in the dispersion;

preparing an aqueous dispersion of the protein;

admixing the active agent with the aqueous dispersion of the protein to provide an active agent/protein dispersion; and admixing the active agent/protein dispersion and the weak acid/volatile divalent metal salt dispersion at a ratio of 1.0:1.5 to 1.5:1.0 to form the spray-drying feedstock solution.

14. The method as claimed in claim 13 in which the spray drying feedstock solution further comprises a hydrocolloid, wherein a dispersion of the hydrocolloid is added to the aqueous solution of the weak acid or added to the active agent/protein dispersion.

15. The method as claimed in claim 13 in which the aqueous solution of the weak acid has a weak acid concentration of 0.2 M-2.2 M.

16. The method as claimed in claim 13 in which the aqueous dispersion of the volatile divalent metal salt has a volatile divalent metal salt concentration of 0.2 M-2.2 M.

17. The method as claimed in claim 13 in which the aqueous dispersion of the protein has a protein concentration of 4.0-15.0 (w/v).

\* \* \* \* \*